United States Patent [19]

Ghosh et al.

[11] Patent Number: 6,090,399
[45] Date of Patent: Jul. 18, 2000

[54] CONTROLLED RELEASE COMPOSITION INCORPORATING METAL OXIDE GLASS COMPRISING BIOLOGICALLY ACTIVE COMPOUND

[75] Inventors: Tirthankar Ghosh, Oreland; Edwin Hugh Nungesser, Horsham, both of Pa.

[73] Assignee: Rohm and Haas Company, Phila., Pa.

[21] Appl. No.: 09/189,479

[22] Filed: Nov. 10, 1998

Related U.S. Application Data

[60] Provisional application No. 60/069,243, Dec. 11, 1997.

[51] Int. Cl.⁷ .............................. A01N 25/08; A01N 25/34
[52] U.S. Cl. ......................... 424/409; 424/405; 424/484
[58] Field of Search .................................... 424/405, 408, 424/409, 484

[56] References Cited

U.S. PATENT DOCUMENTS

| | | | |
|---|---|---|---|
| 4,783,221 | 11/1988 | Grove | 106/18.22 |
| 5,591,453 | 1/1997 | Ducheyne et al. | 424/484 |
| 5,683,720 | 11/1997 | Myers et al. | 424/489 |
| 5,912,286 | 6/1999 | Griffith et al. | 524/83 |

FOREIGN PATENT DOCUMENTS

| | | |
|---|---|---|
| 0747184A2 | 12/1996 | European Pat. Off. . |
| 0832 561A2 | 4/1998 | European Pat. Off. . |
| 4329279C | 5/1996 | Germany . |
| 7-291804 | 4/1994 | Japan . |
| 6-271792 | 9/1994 | Japan . |

*Primary Examiner*—Thurman K. Page
*Assistant Examiner*—Isis Ghali
*Attorney, Agent, or Firm*—S Mathew Cairns; Thomas D. Rogerson

[57] ABSTRACT

Disclosed are compositions containing biologically active compounds that slowly release the biologically active compound. These compositions may be directly incorporated into the locus to be protected or may be applied to a structure in a coating.

15 Claims, No Drawings

CONTROLLED RELEASE COMPOSITION INCORPORATING METAL OXIDE GLASS COMPRISING BIOLOGICALLY ACTIVE COMPOUND

This application is a continuation of Provisional Application No. 60/069,243, filed Feb. 11, 1997.

BACKGROUND OF THE INVENTION

This invention relates generally to a composition for controlling the release of microbicidally active compounds. In particular, this invention relates to the use of metal oxide glasses to control the release of microbicidally active compounds.

The ability to control release of biologically active compounds to a locus to be protected is important in the field of microbicidally active compounds. Typically, when a microbicidally active compound is added to a locus to be protected, the compound is rapidly released, whether or not it is needed. Controlled release compositions deliver the biologically active compound in a manner that more closely matches the need for the compound. In this way, only the amount of the biologically active compound needed is released into the locus to be protected. Controlled release offers the advantages of reduced cost, lowered toxicity and increased efficiency.

Various methods of controlled release are known. Such methods include encapsulation of the microbicidally active compound, adsorption of the microbicidally active compound on an inert carrier, such as silica gel, and clathration of the microbicidally active compound.

All of these methods have drawbacks to widespread commercial use, such as expensive starting materials, limited compatibility of the controlled release method to the compounds to be released or locus to be protected, and limited control of the release of the microbicidally active compounds. For example, adsorption of a microbicide on an inert carrier results in a composition that releases the microbicide in a diffusion controlled manner. Such compositions usually do not provide control of the release of the microbicide. Additionally, whether a clathrate forms or not depends on the solvent used, which limits available solvent choices.

U.S. Pat. No. 5,591,453 (Ducheyne et al.) discloses biologically active molecules in a silica based glass to provide controlled release of the biologically active molecules. The biologically active molecules disclosed are all pharmaceutical agents, such as drugs and growth factors. This patent is directed to using these glasses in the acceleration and regeneration of bone tissue and a reduction in the incidence of infection in the area adjacent to the glasses when implanted in a person. There is no discussion of incorporating non-pharmaceutical agents, such as microbicides or agricultural pesticides, into the glasses. This patent teaches that the release of the biologically active molecules is controlled by varying the size of the glass particles from 500 microns to 5 millimeters. Increasing the particle size slows down the release of the biologically active molecules because it takes longer for the biologically active molecule to diffuse out of the particle. This is an inefficient method to control the release of biologically active molecules. Also, the large particle sizes required to slow the release of the biologically active molecules are incompatible with most industrial systems, such as coatings and paints. Large particles, when added to a paint, adversely affect the gloss.

Japanese patent application 07 291 805 A (Yamamoto) discloses agricultural pesticides incorporated into metal oxide glasses prepared from metal alkoxide monomers. The metal alkoxide monomers contain only alkoxy groups. This patent application does not teach modification of the metal oxide glass in order to vary the release rate of the incorporated agricultural pesticide.

There is therefore a continuing need for controlled release compositions of biologically active compounds, such as microbicides, marine antifouling agents and agricultural pesticides, that are inexpensive, compatible in a broad range of loci to be protected, have a small particle size, and more efficient at controlling the release of the biologically active compound than compositions currently available.

SUMMARY OF THE INVENTION

It has now been found that the release of biologically active molecules from a metal oxide glass can be controlled by varying the substituents of the metal alkoxide monomers used to form the glass without varying the size of the glass particles.

The present invention is directed to a controlled release composition including one or more biologically active compounds incorporated into a metal oxide glass having a porous matrix, wherein the biologically active compound is selected from the group consisting of microbicide, marine antifouling agent, and agricultural pesticide; and the metal oxide glass is prepared by polymerizing one or more metal alkoxide monomers of formula (I):

$$(R^2)_n M_1^{+m}(OR^1)_3 \quad (I)$$

optionally in the presence of one or more metal alkoxide monomers of formula (II):

$$(R^5)_y R^4 R^3 M_2^{+x} OR^1 \quad (II)$$

wherein $M_1$ and $M_2$ are independently selected from silicon, aluminum, zirconium, titanium, tin, vanadium, and iron; $R^1$=($C_{1-4}$)alkyl; $R^2$, $R^3$, $R^4$ and $R^5$ are independently selected from $OR^1$, ($C_{1-12}$)alkyl, substituted ($C_{1-12}$)alkyl, ($C_{2-10}$)alkenyl, halosubstituted ($C_{2-10}$)alkenyl, ($C_{3-10}$) alkynyl, halosubstituted ($C_{3-10}$)alkynyl, phenyl, substituted phenyl, ($C_{7-10}$)aralkyl; m and x are independently 3 or 4; n=m-3; and y=x-3; with the proviso that when the biologically active compound is an agricultural pesticide, at least one metal alkoxide monomer of formula (II) is present where $R^3$ or $R^4$ is not $OR^1$.

The present invention is further directed to a controlled release composition including one or more biologically active compounds incorporated into an organo-metal oxide glass having a porous matrix, wherein the biologically active compound is selected from the group consisting of microbicide, marine antifouling agent, and agricultural pesticide; and the organo-metal oxide glass is prepared by polymerizing, in the presence of a hydroxylic compound, one or more metal alkoxide monomers of formula (I):

$$(R^2)_n M_1^{+m}(OR^1)_3 \quad (I)$$

optionally in the presence of one or more metal alkoxide monomers of formula (II):

$$(R^5)_y R^4 R^3 M_2^{+x} OR^1 \quad (II)$$

wherein $M_1$ and $M_2$ are independently selected from silicon, aluminum, zirconium, titanium, tin, vanadium, and iron; $R^1$=($C_{1-4}$)alkyl; $R^2$, $R^3$, $R^4$ and $R^5$ are independently selected from OR', ($C_{1-12}$)alkyl, substituted ($C_{1-12}$)alkyl, ($C_{2-10}$)alkenyl, halosubstituted ($C_{2-10}$)alkenyl, ($C_{3-10}$)

alkynyl, halosubstituted ($C_{3-10}$)alkynyl, phenyl, substituted phenyl, ($C_{7-10}$)aralkyl; m and x are independently 3 or 4; n=m-3; and y=x-3; and wherein the hydroxylic compound is selected from the group consisting of ($C_{4-20}$)alkyl alcohols; ($C_{7-10}$)aralkyl alcohols, ($C_{2-20}$)glycols, poly(ethylene glycol) alkyl ethers, poly(ethylene glycol) aralkyl ethers, and poly(ethylene glycol) aryl ethers.

The present invention is also directed to a method of controlling the release of biologically active compounds including the step of incorporating the biologically active compounds in a metal oxide glass having a porous matrix, wherein the biologically active compound is selected from the group consisting of microbicide, marine antifouling agent, and agricultural pesticide; and the metal oxide glass is prepared by polymerizing one or more metal alkoxide monomers of formula (I):

$$(R^2)_n M_1^{+m}(OR^1)_3 \qquad (I)$$

optionally in the presence of one or more metal alkoxide monomers of formula II $$(R^5)_y R^4 R^3 M_2^{+x} OR^1 \qquad (II)$$

wherein $M_1$ and $M_2$ are independently selected from silicon, aluminum, zirconium, titanium, tin, vanadium, and iron; $R^1$=($C_{1-4}$)alkyl; $R^2$, $R^3$, $R^4$ and $R^5$ are independently selected from $OR^1$, ($C_{1-12}$)alkyl, substituted ($C_{1-12}$)alkyl, ($C_{2-10}$)alkenyl, halosubstituted ($C_{2-10}$)alkenyl, ($C_{3-10}$)alkynyl, halosubstituted ($C_{3-10}$)alkynyl, phenyl, substituted phenyl, ($C_{7-10}$)aralkyl; m and x are independently 3 or 4; n=m-3; and y=x-3; with the proviso that when the biologically active compound is an agricultural pesticide, at least one metal alkoxide monomer of formula (II) is present where $R^3$ or $R^4$ is not $OR^1$.

The present invention is also directed to a method of controlling the release of biologically active compounds including the step of incorporating the biologically active compounds in an organo-metal oxide glass having a porous matrix, wherein the biologically active compound is selected from the group consisting of microbicide, marine antifouling agent, and agricultural pesticide; and wherein the organo-metal oxide glass is prepared by polymerizing, in the presence of a hydroxylic compound, one or more metal alkoxide monomers of formula (I):

$$(R^2)_n M_1^{+m}(OR^1)_3 \qquad (I)$$

optionally in the presence of one or more metal alkoxide monomers of formula II $$(R^5)_y R^4 R^3 M_2^{+x} OR^1 \qquad (II)$$

wherein $M_1$ and $M_2$ are independently selected from silicon, aluminum, zirconium, titanium, tin, vanadium, and iron; $R^1$=($C_{1-4}$)alkyl; $R^2$, $R^3$, $R^4$ and $R^5$ are independently selected from $OR^1$, ($C_{1-12}$)alkyl, substituted ($C_{1-12}$)alkyl, ($C_{2-10}$)alkenyl, halosubstituted ($C_{2-10}$)alkenyl, ($C_{3-10}$)alkynyl, halosubstituted ($C_{3-10}$)alkynyl, phenyl, substituted phenyl, ($C_{7-10}$)aralkyl; m and x are independently 3 or 4; n=m-3; and y=x-3; and wherein the hydroxylic compound is selected from the group consisting of ($C_{4-20}$)alkyl alcohols; ($C_{7-10}$)aralkyl alcohols; ($C_{2-20}$)glycols; poly(ethylene glycol) alkyl ethers; poly(ethylene glycol) aralkyl ethers; and poly(ethylene glycol) aryl ethers.

The present invention is also directed to a method of controlling or inhibiting the growth of pests at a locus comprising introducing into or onto the locus to be protected an effective amount of the compositions described above.

DETAILED DESCRIPTION OF THE INVENTION

As used throughout the specification, the following terms shall have the following meanings, unless the context clearly indicates otherwise.

The term "biologically active compound" refers to a microbicide, a marine antifouling agent, or an agricultural pesticide. The terms "microbicidally active compound" and "microbicide" refer to a compound capable of inhibiting or controlling the growth of microorganisms at a locus. The term "microorganism" includes, but is not limited to, industrial fungi, bacteria, and algae. The term "locus" refers to an industrial system or product subject to contamination by microorganisms. The term "pest" refers to agricultural and industrial fungi, bacteria, algae, insects, mites, and weeds.

"Marine antifouling agent" includes algaecides and molluscicides. "Marine antifouling activity" is intended to include both the elimination of and inhibition of growth of marine organisms. Marine organisms controlled by marine antifouling agents suitable for use in this invention include both hard and soft fouling organisms. Generally speaking, the term "soft fouling organisms" refers to plants and invertebrates, such as slime, algae, kelp, soft corals, tunicates, hydroids, sponges, and anemones, while the term "hard fouling organisms" refers to invertebrates having some type of hard outer shell, such as barnacles, tubeworms, and molluscs.

"Agricultural pesticides" include agricultural fungicides, herbicides, insecticides and miticides. "Agricultural fungicide" refers to a compound capable of inhibiting the growth of or controlling the growth of fungi in an agricultural application, such as treatment of plants and soil; "herbicide" refers to a compound capable of inhibiting the growth of or controlling the growth of certain plants; "insecticide" refers to a compound capable of controlling insects; and "miticide" refers to a compound capable of controlling mites.

The term "alkyl" means a linear, branched, cyclic, or any combination thereof hydrocarbon. "Substituted alkyl" means one or more of the hydrogens on the alkyl group are replaced by another substituent, such as cyano, ($C_{1-4}$)alkyl, nitro, mercapto, ($C_{1-4}$)alkylthio, halo, ($C_{1-6}$)alkylamino, ($C_{1-6}$)dialkylamino, ($C_{1-6}$)alkoxy, and tri($C_{1-4}$)alkoxysilyl. "Aralkyl" means an alkyl group having one of its hydrogens replaced by an aryl group. "Substituted phenyl" mean one or more of the hydrogens on the aromatic ring are replaced by another substituent, such as cyano, ($C_{1-4}$)alkyl, nitro, mercapto, ($C_{1-4}$)alkylthio, halo, ($C_{1-6}$)alkylamino, ($C_{1-6}$)dialkylamino, and ($C_{1-4}$)alkoxy. "Halo" means fluoro, chloro, bromo, and iodo. The term "metal oxide glass" means a polymer prepared by the hydrolysis of metal alkoxide monomers and having metal-oxygen-metal bonds. All amounts are percent by weight unless otherwise noted and all percent by weight ranges are inclusive. All ratios are by weight unless otherwise specified. All ratio ranges are inclusive. As used throughout the specification, the following abbreviations are applied: g=gram; mL=milliliter; μm=micrometer; MW=molecular weight; HPLC=high performance liquid chromatography; ppm=parts per million; and wt %=percent by weight.

The biologically active compounds useful in the present invention are those which are hydrogen bond acceptors. That is, the compounds are those having one or more atoms selected from nitrogen, oxygen, fluorine or mixtures thereof The nitrogen or oxygen may have single or multiple bonds, such as in a carbonyl, imine, nitrile, hydroxy, amide, alkoxy, ester, ether or amine group.

Suitable microbicides of the present invention include, but are not limited to: methylenebis(thiocyanate); isothiazolones; carbamates; heterocyclic compounds; carboxylic acids and their derivatives; amines, ammonium and phosphonium salts; aldehydes, ketones and formaldehyde releasers; halogenated aromatic or aliphatic compounds; alkenes; and mixtures thereof Examples of isothiazolones include but are not limited to: 2-n-octyl-3-isothiazolone; 4,5-dichloro-2-n-octyl-3-isothiazolone; 4,5-dichloro-2-cyclohexyl-3-isothiazolone; 5-chloro-2-methyl-3-isothiazolone; 2-methyl-3-isothiazolone; 1,2-benzisothiazolin-3-one; and 2-methyl-4,5-trimethylene-3-isothiazolone. Examples of carbamates include but are not limited to: 3-iodo-2-propynyl butyl carbamate; methyl benzimidazol-2-ylcarbamate; imidazoli dinyl urea; diazolidinyl urea; N'-[3,4-dichlorophenyl]-N,N-dimethylurea; 3,4,4'-trichlorocarbanilide; dimethyl dithiocarbamate; and disodium ethylene bisdithiocarbamate. Examples of heterocyclic compounds include but are not limited to: zinc 2-pyridinethiol-1-oxide; sodium 2-pyridinethiol-1-oxide; 10,10'-oxybisphenoxyarsine; N-trichloromethylthiophthalimide; 5- oxo-3,4-dichloro-1,2-dithiol; 3-bromo-1-chloro-5,5-dimethylhydantoin; 4,4-dimethyl- 1,3-dimethylolhydantoin; 2-(thiocyanomethylthio)benzothiazole; 2- methylthio-4-t-butylamino-6-cyclopropylamino-s-triazine; iodopolyvinylpyrrolidone; 3,5-dimethyl-1H-pyrazole-1- methanol; 1-(2-hydroxyethyl)-2-octadecylimidazoline; 4-(2-nitrobutyl)-morpholine; triazine; N,N'-methylenebis(5-methyl- 1,3-oxazolidine); 2,2'-oxybis(4,4, 6-trimethyl- 1,3,2-dioxaborinane); 2,2'-(1-methyltrimethylene-dioxy) bis(4-ethyl- 1,3,2-dioxaborinane); hexahydro- 1,3,5-tris(2-hydroxyethyl)-s-triazine; 4,4-dimethyloxazolidine; 3,4,4'-trimethyloxazolidine; 4,4'-(2-ethyl-nitrotrimethylene)dimorpholine; 2-methylthio-4-t-butylamino-6-cyclopropyl-amino-s-triazine; 2,3,5,6-tetrachloro-4- (methylsulfonyl)pyridine; alpha-[2-(4-chlorophenyl)ethyl] -alpha-(1,1-dimethylethyl)-1H-1,2,4-triazolyl-(1)-ethanol; 1[(2-(2',4'-dichlorophenyl)-4-propyl-1,3-dioxolan-2-yl-methyl]-1H-1,2,4-triazoyl; didecyldim-ethylammonium chloride; copper-8-hydroxyquinoline; 1-[2-(2,4-dichlorophenyl)-1,3-dioxolan-2-yl-methyl]-1H-1,2, 4-triazole; 2-(4-thiazolyl)-benzimidazole; 3,5-dimethyl-1,3, 5-thiadiazine-2-thione; 2-chloro-4,6-bis(ethylamino)-1,3,5-triazine; 2-chloro-4-ethylamino-6-tert-butylamino-1,3,5-triazine; 1-(3-chloroallyl)-3,5,7-triaza-1-azoniaadamantane chloride; copper naphthenate; 5-hydroxymethoxymethyl-1-aza-3,7-dioxabicyclo [3.3.0]octane; 5-hydroxymethyl-1-aza-3,7-dioxabicyclo[3.3.0]octane; 7-ethyl-1, 5-dioxa-3-azabicyclooctane; cetylpyridinium chloride; 3-bromo-1-chloro-5-dimethyl-5-ethylhydantoindodecyl-di(aminoethyl)-glycine; and 5-hydroxypoly-[methyleneoxyethyl]methyl-1-aza-3,7-dioxabicyclo[3.3.0] octane. Examples of carboxylic acids and their derivatives include but are not limited to:(E,E)-2,4-hexadienoic acid; benzoic acid; sodium or calcium propionate; ethylenediaminetetraacetic acid disodium salt; and sodium hydroxymethylglycinate; benzyl ester of 4-hydroxybenzoic acid; ($C_{1-4}$)alkyl esters of 4-hydroxybenzoic acid; ($C_{1-4}$)alkyl esters of 4-hydroxybenzoic acid sodium salts; dimethylamide of tall oil fatty acids; and 2,2-dibromo-3-nitrilopropionamide. Examples of amines include but are not limited to: 1-(alkylamino)-3-amino-propane; 2-hydroxypropyl methanethiosulfonate; p-nitrophenol; and 4-chloro-3,5-dimethylphenol. Examples of ammonium and phosphonium salts include but are not limited to: n-alkyl dimethyl benzylammonium chloride; cetyltrimethylammonium chloride; didecyldimethylammonium chloride; poly (hexamethylenebiguanide) hydrochloride; poly[oxyethylene (dimethyliminio) ethylene(dimethyliminio)-ethylene dichloride]; alkyl dimethyl dichlorobenzylammonium chloride; dodecylguanidine hydrochloride; 2-(decylthio) ethaneamine hydrochloride; quaternary ammonium compounds; tetrakis(hydroxymethyl)phosphonium chloride; and tetrakis(hydroxymethyl)phosphonium sulfate. Examples of aldehydes, ketones and formaldehyde releasers include but are not limited to: pentane-1,5-dial; 1,2-benzenedicarboxaldehyde; formaldehyde; 2-bromo-4'-hydroxyacetophenone; tris(hydroxymethyl)nitromethane; and 5-bromo-5-nitro-1,3-dioxane. Examples of haolgenated aromatic compounds include but are not limited to: 2,4,5, 6-tetrachloroisophthalonitrile; 2,4,4'-trichloro-2'-hydroxydiphenyl ether; 2,2'-dihydroxy-5,5'-dichloro-diphenylmethane; and 1,6-di-(4'-chlorophenyldiguanide)-hexane. Examples of halogenated aliphatic compounds include but are not limited to: 1,2-dibromo-2,4-dicyanobutane; diiodomethyl-p-tolysulfone; dibromonitro-ethane; and hexachlorodimethylsulfone. Examples of alkenes include but are not limited to: b-bromo-b-nitrostyrene; 1,4-bis(bromoacetoxy)-2-butene; terpene; and limonene.

Suitable marine antifouling agents of the present invention include, but are not limited to: manganese ethylenebisdithiocarbamate; zinc dimethyl dithiocarbamate; 2-methyl-4-t-butylamino-6-cyclopropylamino-s-triazine; 2,4,5,6-tetrachloroisophthalonitrile; N,N-dimethyl dichlorophenyl urea; zinc ethylenebisdithiocarbamate; copper thiocyanate; 4,5-dichloro-2-n-octyl-3-isothiazolone; N-(fluorodichloromethylthio)-phthalimide; N,N-dimethyl-N'-phenyl-N'-fluorodichloromethylthio-sulfamide; zinc 2-pyridinethiol-1-oxide; tetramethylthiuram disulfide; 2,4,6-trichlorophenylmaleimide; 2,3,5,6-tetrachloro-4-(methylsulfonyl)-pyridine; 3-iodo-2-propynyl butyl carbamate; duiodomethyl p-tolyl sulfone; bis dimethyl dithiocarbamoyl zinc ethylenebisdithiocarbamate; phenyl (bispyridil) bismuth dichloride; 2-(4-thiazolyl) benzimidazole; pyridine triphenyl borane; phenylamides; halopropargyl compounds; and 2-haloalkoxyaryl-3-isothiazolones. Suitable 2-haloalkoxyaryl-3-isothiazolones include, but are not limited to: 2-(4-trifluoromethoxyphenyl)-3-isothiazolone, 2-(4-trifluoromethoxyphenyl)-5-chloro-3-isothiazolone, and 2-(4-trifluoromethoxyphenyl)-4,5-dichloro-3-isothiazolone.

Suitable agricultural fungicides of the present invention include, but are not limited to: dithiocarbamate and derivatives such as ferbam, ziram, maneb, mancozeb, zineb, propineb, metham, thiram, the complex of zineb and polyethylene thiuram disulfide, dazomet, and mixtures of these with copper salts; nitrophenol derivatives such as dinocap, binapacryl, and 2-sec-butyl-4,6-dinitrophenyl isopropyl carbonate; heterocyclic structures such as captan folpet, glyodine, dithianon, thioquinox, benomyl, thiabendazole, vinolozolin, iprodione, procymidone, triadimenol, triadimefon, bitertanol, fluoroimide, triarimol, cycloheximide, ethirimol, dodemorph, dimethomorph, thifluzamide, and, quinomethionate; miscellaneous halogenated fungicides such as chloranil, dichlone, chloroneb, tricamba, dichloran, and polychloronitrobenzenes; fungicidal antibiotics such as griseofulyin, kasugamycin and streptomycin; miscellaneous fungicides such as diphenyl sulfone, dodine, methoxyl, 1-thiocyano-2,4-dinitrobenzene, 1-phenylthiosemicarbazide, thiophanate-methyl, and cymoxanil; as well as acylalanines such as furalaxyl, cyprofuram, surface, benalaxyl, and oxadixyl; fluazinam; flumetover; phenylbenzamide derivatives such as those disclosed in EP 578586 A1; amino acid derivatives such as valine derivatives disclosed in EP 550788 A1; methoxyacrylates such as methyl (E)-2-(2-(6-(2-cyanophenoxy) pyrimidin-4-yloxy)phenyl)-3-methoxyacrylate; benzo(1,2, 3)-thiadiazole-7-carbothioic acid S-methyl ester; propamocarb; imazalil; carbendazim; myclobutanil; fenbuconazole; tridemorph; pyrazophos; fenarimol; fenpiclonil; and pyrimethanil.

Suitable herbicides of the present invention include, but are not limited to: carboxylic acid derivatives, including benzoic acids and their salts; phenoxy and phenyl substituted carboxylic acids and their salts; and trichloroacetic acid and its salts; carbamic acid derivatives, including ethyl N,N-di(n-propyl)-thiolcarbamate and pronamide; substituted ureas; substituted triazines; diphenyl ether derivatives such as oxyfluorfen and fluoroglycofen; anilides such as propanil; oxyphenoxy herbicides; uracils; nitriles; and other organic herbicides such as dithiopyr and thiazopyr.

Suitable insecticides of the present invention include, but are not limited to: acephate; aldicarb; alpha-cypermethrin; azinbhos-methyl; bifenthrin; binapacryl; buprofezin; carbaryl; carbofuran; cartap; chlorpyrifos; chlorpyrifos methyl; clofentezine; cyfluthrin; cyhexatin; cypermethrin; cyphenothrin; deltamethrin; demeton; demeton-S-methyl; demeton-O-methyl; demeton-S; demeton-S-methyl sulfoxid; demephion-O; demephion-S; dialifor; diazinon; dicofol; dicrotophos; diflubenzuron; dimethoate; dinocap; endosulfan; endothion; esfenvalerate; ethiofencarb; ethion; ethoatemethyl; ethoprop; etrimfos; fenamiphos; fenazaflor; fenbutatin-oxide; fenitrothion; fenoxycarb; fensulfothion; fenthion; fenvalerate; flucycloxuron; flufenoxuron; fluyalinate; fonofos; fosmethilan; furathiocarb; hexythiazox; isazophos; isofenphos; isoxathion; methamidophos; methidathion; methiocarb; methomyl; methyl parathion; mevinphos; mexacarbate; monocrotophos; nicotine; omethoate; oxamyl; parathion; permethrin; phorate; phosalone; phosmet; phosphamidon; pirimicarb; pirimiphosethyl; profenofos; promecarb; propargite; pyridaben; resmethrin; rotenone; tebufenozide; temephos; TEPP; terbufos; thiodicarb; tolclofos-methyl; triazamate; triazophos and vamidothion.

The biologically active compound is preferably a microbicide or a marine antifouling agent. It is preferred that the microbicides are selected from: 5-chloro-2-methyl-3-isothiazolone; 2-methyl-3-isothiazolone; 2-n-octyl-3-isothiazolone; 4,5-dichloro-2-n-octyl-3-isothiazolone; 4,5-dichloro-2-cyclohexyl-3-isothiazolone; 4,5-dichloro-2-cyclohexyl-3-isothiazolone; 3-iodo-2-propynyl butyl carbamate; 1,2-dibromo-2,4-dicyanobutane; methylene-bisthiocyanate; 2-thiocyanomethylthiobenzothiazole; 2,4,5, 6-tetrachloroisophthalonitrile; 5-bromo-5-nitro-1,3-dioxane; 2,2-dibromo-3-nitrilopropionamide; 3-bromo-1-chloro-5,5-dimethylhydantoin; 1,2-benzisothiazolin-3-one; 2-methyl-4,5-trimethylene-3-isothiazolone; and 3,4,4'-trichlorocarbanilide. It is especially preferred that the microbicides are selected from: 2-methyl-3-isothiazolone; 5-chloro-2-methyl-3-isothiazolone; 2-n-octyl-3-isothiazolone; 4,5-dichloro-2-n-octyl-3-isothiazolone; 4,5-dichloro-2-cyclohexyl-3-isothiazolone; 1,2-benzisothiazolin-3-one; 2-methyl-4,5-trimethylene-3-isothiazolone; 3-iodo-2-propynyl butyl carbamate; and 3,4, 4'-trichlorocarbanilide.

Combinations of microbicides, marine antifouling agents, agricultural pesticides or mixtures thereof may be used advantageously in the compositions of the present invention, as long as the biologically active compounds do not react with or otherwise destabilize each other, and are compatible with the metal oxide glass. This has the advantage of controlling the release of multiple biologically active compounds which may provide a broader spectrum of control than one microbicide alone. Also, this may reduce the cost of treatment when multiple biologically active compounds must be used. When more than one biologically active compound is used, the weight ratio of the total amount of the biologically active compound to the metal oxide glass is generally from 0.1:99.9 to 75:25. When used in combination, the biologically active compounds may be combined in any weight ratio from 0.1:99.9 to 99.9:0.1.

The amount of biologically active compounds useful in the present invention is 0.1 to 75 wt %, based on the total weight of the composition. It is preferred that the amount of biologically active compound is 5 to 60 wt %, and more preferably 10 to 50 wt %.

The metal oxide glasses useful in the present invention are those prepared by polymerizing one or more metal alkoxide monomers of formula (I):

$$(R^2)_n M_1^{+m} (OR^1)_3 \qquad (I)$$

optionally in the presence of one or more metal alkoxide monomers of formula (II):

$$(R^5)_y R^4 R^3 M_2^{+x} OR^1 \qquad (II)$$

wherein $M_1$ and $M_2$ are independently selected from silicon, aluminum, zirconium, titanium, tin, vanadium, and iron; $R^1=(C_{1-4})$alkyl; $R^2$, $R^3$, $R^4$ and $R^5$ are independently selected from )$R^1$, $(C_{1-12})$alkyl, substituted $(C_{1-12})$alkyl, $(C_{2-10})$alkenyl, halosubstituted $(C_{2-10})$alkenyl, $(C_{3-10})$alkynyl, halosubstituted $(C_{3-10})$alkynyl, phenyl, substituted phenyl, $(C_{7-10})$aralkyl; m and x are independently 3 or 4; n=m-3; and y=x-3. It is preferred that the alkyl groups are methyl and ethyl. It is preferred that the aralkyl groups are benzyl and phenethyl. The preferred metal alkoxide monomers of formulae (I) and (II) are those wherein M is silicon, aluminum or zirconium, and more preferably silicon. Mixtures of metal alkoxide monomers containing different metals may be used advantageously in the present invention. For example, a mixture of silicon alkoxide monomers and aluminum alkoxide monomers may be used. When mixtures of metal alkoxide monomers are used, they may be used in any weight ratio from 1:99 to 99:1. The range of weight ratios of mixtures of metal alkoxide monomers is preferably 10:90 to 90:10, and more preferably 20:80 to 80:20. Metal alkoxide monomers useful in the present invention are generally commercially available from Gelest, Inc. (Tullytown, Pa.), and may be used without further purification.

The metal alkoxide monomers of formula (II) useful in the present invention have one or more alkoxy groups. It is preferred that the monomers of formula II have two or more alkoxy groups. At least one metal alkoxide monomer of formula I must be used to prepare the compositions of the present invention in order to provide sufficient crosslinking of the resulting metal oxide glass. If the metal oxide glass has insufficient crosslinking, the release of the biologically active compounds from the glass will not be effectively controlled. For example, a metal oxide glass prepared from dimethylsiloxane as the only metal alkoxide monomer does not provide sufficient controlled release because it contains insufficient alkoxide groups to provide crosslinking. Mixtures of metal alkoxide monomers containing different numbers of alkoxy groups are useful in the present invention. This has the advantage of providing metal oxide glasses with a mixture of crosslinking, which may provide variable rates of release of the biologically active compounds.

When a metal alkoxide monomer of formula (I) having only alkoxy groups (that is, $R^2=OR^1$) is used to prepare the compositions of the present invention, it is preferred that a second metal alkoxide monomer having at least one group that is not alkoxy be used in combination. For example, particularly useful combinations of metal alkoxide monomers include tetramethoxy orthosilicate or tetraethoxy orthosilicate with methyltriethoxy orthosilicate, methyltrimethoxy orthosilicate, phenyltriethoxy orthosilicate, octyltriethoxy orthosilicate, or dimethyldiethoxy orthosilicate.

When the biologically active compound is an agricultural pesticide, particularly useful compositions of the present invention comprise at least one monomer having at least one group that is not an alkoxy group.

Suitable metal alkoxide monomers useful in preparing the compositions of the present invention include, but are not limited to: tetramethoxy orthosilicate, tetraethoxy orthosilicate, methyltriethoxy orthosilicate, methyltrimethoxy orthosilicate, phenyltriethoxy orthosilicate, octyltriethoxy orthosilicate, phenyltrimethoxy orthosilicate, dimethyldiethoxy orthosilicate, bis(trimethoxysilyl)methane, bis(triethoxysilyl)ethane, bis(trimethoxysilyl)hexane, 3-butenyltriethoxy silane, methacryloxypropyl triethoxysilane, methacryloxypropyl trimethoxysilane, triethoxyaluminum, methyldiethoxyaluminum, triisopropoxyaluminum, tetraethoxyzirconium, methyltriethoxyzirconium, tetranbutoxyzirconium, tetra-t-butoxyzirconium, tetramethoxytin, tetraethoxytin, tetramethoxyvanadium, tetraethoxyvanadium, tetraethoxytitanium, tetramethoxytitanium, tetraethoxyiron, and mixtures thereof. The metal alkoxide monomers are preferably: tetramethoxy orthosilicate, tetraethoxy orthosilicate, methyltriethoxy orthosilicate, methyltrimethoxy orthosilicate, phenyltriethoxy orthosilicate, octyltriethoxy orthosilicate, dimethyldiethoxy orthosilicate, triethoxyaluminum, triusopropoxyaluminum, tetraethoxyzirconium, tetra-n-butoxyzirconium, tetra-t-butoxyzirconium, and mixtures thereof. The metal alkoxide monomers are more preferably: tetramethoxy orthosilicate, tetraethoxy orthosilicate, methyltriethoxy orthosilicate, methyltrimethoxy -orthosilicate, phenyltriethoxy orthosilicate, octyltriethoxy orthosilicate, dimethyldiethoxy orthosilicate, and mixtures thereof.

The compositions of the metal oxide glasses of the present invention are either solids or liquids. The solid compositions of this invention may be added to a locus directly. In certain loci, such as paints, it is preferred to grind the solid compositions to provide smaller particles before adding the compositions to the locus. As the metal oxide glasses of the present invention are glasses, once the solid glass has formed, it cannot be dissolved in a solvent. The compositions of the present invention, when used as a liquid before removing any water and alcohol, may be added directly to a locus to be protected, such as wood or wood products, or may be formulated in any of a variety of ways. For example, the liquid compositions may be formulated as emulsions; emulsive concentrates; microemulsions; and microemulsive concentrates. The liquid compositions may also be combined with one or more solvents, such as $(C_{1-6})$alcohols; or plasticizers, such as diisodecylphthalate. It is preferred that a plasticizer be combined with the liquid formulation for use in plastics.

The hydroxylic compounds useful in the present invention are any which contain at least one hydroxyl group. Suitable hydroxylic compounds are selected from the group consisting of $(C_{4-20})$alkyl alcohols; $(C_{7-10})$aralkyl alcohols; $(C_{2-20})$glycols; poly(ethylene glycol) alkyl ethers; poly (ethylene glycol) aralkyl ethers; and poly(ethylene glycol) aryl ethers. Suitable hydroxylic compounds include, but are not limited to: hexanol, octanol, decanol, dodecanol, benzyl alcohol, phenyl ethanol, ethylene glycol, propylene glycol, didthylene glycol, dipropylene glycol, poly(ethylene glycol), polypropylene glycol), poly(ethylene glycol) methyl ether, poly(ethylene glycol) benzyl ethers, and poly (ethylene glycol) phenyl ethers. It is preferred that the hydroxylic compounds are hexanol, octanol, decanol, dodecanol, benzyl alcohol, phenyl ethanol, $(C_{3-15})$glycols, and poly(ethylene glycol) methyl ether. The average molecular weights of the poly(ethylene glycol) methyl ethers are preferably from 200 to 10,000, more preferably 350 to 5,000. Hydroxylic compounds having a boiling of 250° C. or greater are especially preferred as they have low volatile organic compound ("VOC") content.

Particularly useful hydroxylic compounds in the compositions of the present invention are those that have microbicidal activity. Such hydroxylic compounds have the added advantage of imparting microbicidal activity to the organometal oxide glass itself. Suitable hydroxylic compounds having microbicidal activity include, but are not limited to: 2-bromo-2-nitropropanediol; 2-hydroxymethylaminoethanol; benzyl alcohol, and n-2-hydroxypropylaminomethanol.

The amount of hydroxylic compound useful in the compositions of the present invention is 1 to 99 wt %, based on the weight of the composition. The amount of hydroxylic compound is preferably 10 to 90 wt %, and more preferably 15 to 70 wt %. A particularly useful amount of hydroxylic compound is 50 wt %. The hydroxylic compounds are generally commercially available, for example from Aldrich Chemical Company (Milwaukee, Wis.), and may be used without further purification.

When glycols are used as the hydroxylic compound, they crosslink with the metal alkoxide monomers. Such crosslinking may be advantageous in situations where organic spacers are desired in the final glass. When alcohols or poly(ethylene glycol) methyl ethers are used as the hydroxylic compound, no crosslinking occurs between the hydroxylic compound and the metal alkoxide monomer. One of the advantages of using alcohols or poly(ethylene glycol) methyl ethers as the hydroxylic compound is that the resulting organo-metal glass contains the hydroxylic compound as a pendant group. These pendant hydroxylic compounds allow for a wider range of formulation possibilities of the organo-metal oxide glasses than are possible with the solid metal oxide glasses of the present invention.

The compositions of the organo-metal oxide glasses of the present invention are either liquids or liquefiable solids. When glycols are used, the organo-metal oxide glasses are mostly solids. When lower molecular weight alcohols and poly(ethylene glycol) methyl ethers are used, the organometal oxide glasses are liquids or solids. The organo-metal oxide glasses are solids when higher molecular weight alcohols and poly(ethylene glycol) methyl ethers are used. For example, when a poly(ethylene glycol) methyl ether having an average molecular weight of 350 is used, the resulting organo-metal oxide glass is a low melting solid, whereas the glass is a solid when a poly(ethylene glycol) methyl ether having an average molecular weight of 750 is used.

The liquid compositions of the organo-metal glasses of the present invention may be added directly to a locus to be protected or may be formulated in any of a variety of ways. For example, the liquid compositions may be formulated as emulsions; emulsive concentrates; microemulsions; and microemulsive concentrates. The liquid compositions may also be combined with one or more solvents, such as $(C_{1-6})$alcohols; or plasticizers, such as diisodecylphthalate. It is preferred that a plasticizer be combined with the liquid formulation for use in plastics. The solid compositions of the organo-metal oxide glasses may be added directly to a locus to be protected, combined with an appropriate solvent, or liquefied by heating of the glass. Once liquefied, the organo-metal glass can be formulated in the same was as a liquid.

An advantage of the compositions of the present invention is that the release rate of the biologically active compounds incorporated into the metal oxide glasses can be controlled by varying the substituents on the metal alkoxide monomers. Biologically active compounds that are basic are released more slowly from metal oxide glasses prepared from metal oxide monomers having only alkoxy groups. Incorporating monomers having a group that is not an alkoxy group in the metal oxide increases the rate of release of basic biologically active compound. For biologically active compounds that are acidic, increasing the proportion of metal oxide monomer that does not have an alkoxy group decreases the rate of release.

The sol-gel process useful in the present invention is well known to those skilled in the art. The metal alkoxide monomer and the biologically active compound to be encapsulated are combined. Water and a catalyst are then added. The amount of water is generally 2 moles per mole of the metal alkoxide. The catalyst is typically added in an amount of 0.00001 moles per mole of the metal alkoxide. The mixture is sealed and allowed to react at a temperature of 15° to 70° C. for a period of 1 hour to 5 days. Once the reaction is complete, any remaining water as well as the alcohol produced during the reaction are removed, yielding a gel, as either a viscous liquid or a solid. The shorter the time period during which the water and alcohol is removed, the slower the release rate of the biologically active compound from the resulting metal oxide glass.

Optionally, a solvent may be added to the reaction mixture. The solvent may be any solvent which is compatible with the metal alkoxide and the compound to be encapsulated, is miscible with water, and is easily removable or compatible with the final product. It is preferred to use a solvent. Suitable solvents include, but are not limited to $(C_{1-4})$alcohols, such as methanol, ethanol, propanol, isopropanol, and butanol. Methanol and ethanol are preferred. Mixtures of solvents may also be used.

When the hydroxylic compounds of the present invention are used, they may be added to the reaction at any time prior to the complete removal of the water and alcohol. The hydroxylic compound is preferably used as the solvent or added to the reaction just prior to the step of removing the water and alcohol. When used as the solvent, the hydroxylic compounds may be used to dissolve the biologically active compound and then combined with the metal alkoxide monomer.

The catalyst useful in the sol-gel process of the present invention is either an acid or a base. Suitable acid catalysts include, but are not limited to: mineral acids, such as hydrochloric acid, nitric acid, and sulfuric acid; and organic acids. Suitable base catalysts include, but are not limited to: inorganic bases, such as potassium hydroxide, sodium hydroxide, calcium hydroxide, and ammonia; and organic bases, such as triethylamine, trimethylamine, triisopropylamine, ethylenediamine, pyridine, and piperidine. It is preferred to use an acid catalyst, and more preferably mineral acids.

When the sol-gel reaction is carried out under basic (pH>7) conditions, the release of the biologically active compound is faster than when the comparable reaction is carried out under acidic conditions. It is preferred to carry out the sol-gel reaction under acidic conditions (pH<7).

The sol-gel reaction can occur at a temperature of 15° to 70° C. It is preferred to run the reaction at a temperature of 20° to 40° C. The reaction is typically complete within 1 hour to 5 days. It is preferred to react the mixture for 2 hours to 3 days. The reaction time is related, in part, to the temperature of the reaction. Therefore, lower reaction temperatures generally result in longer reaction times. When hydroxylic compounds are used to prepare the organo-metal oxide glasses of the present invention, the sol-gel reaction can occur at higher temperatures, for example at 25° to 120° C. The upper temperature is limited only by the boiling point of the hydroxylic compound and the boiling point or decomposition point of the biologically active compound. The use of a higher temperature is advantageous in reducing reaction times.

The metal oxide glass and organo-metal oxide glass compositions of the present invention may optionally contain inert material, such as additional controlled releasing agents, dispersants, pigments, and compatiblizers. Suitable inert material includes, but is not limited to: metal hydroxides, such as zirconium hydroxide and aluminum hydroxide; metal carbonates; metal oxides, such as titanium dioxide; polyphenolic compounds, such as cresol and phenyl-formaldehyde condensates having molecular weights of 500 to 5000; and polysaccharides. The amount of inert material useful in the compositions of the present invention is 1 to 90 wt %, and preferably 20 to 80 wt %. The inert material may be added to the compositions of the present invention at any time during their preparation. It is preferred that the inert material be added to the reaction vessel at the end of the polymerization.

The controlled release compositions of the present invention are useful in controlling or inhibiting the growth of microorganisms in any locus where the biologically active compound alone would be useful. The compositions of this invention are suitable for use in any locus requiring protection from microorganisms. Suitable loci include, but are not limited to: cooling towers; air washers; boilers; mineral slurries; wastewater treatment; ornamental fountains; reverse osmosis filtration; ultrafiltration; ballast water; evaporative condensers; heat exchangers; pulp and paper processing fluids; plastics; emulsions and dispersions; paints; marine antifoulant paints; latexes; coatings, such as varnishes; construction products, such as mastics, caulks, and sealants; construction adhesives, such as ceramic adhesives, carpet backing adhesives, and laminating adhesives; industrial or consumer adhesives; photographic chemicals; printing fluids; household products, such as bathroom disinfectants or sanitizers; cosmetics and toiletries; shampoos; soaps; detergents; industrial disinfectants or sanitizers, such as cold sterilants, hard surface disinfectants; floor polishes; laundry rinse water; metalworking fluids; conveyor lubricants; hydraulic fluids; leather and leather products; textiles; textile products; wood and wood products, such as plywood, chipboard, flakeboard, laminated beams, oriented strandboard, hardboard, and particleboard; petroleum processing fluids; fuel; oilfield fluids, such as injection water, fracture fluids, and drilling muds; agriculture adjuvant preservation; surfactant preservation; medical devices; diagnostic reagent preservation; food preservation, such as plastic or paper food wrap; pools or spas; plants; soil; and seed treatments. It is preferred that the loci are paints; marine antifoulant paints; latexes; plastics; wood and wood products.

The controlled release organo-metal oxide glass compositions of the present invention are particularly useful in controlling or inhibiting the growth of microorganisms in paints, such as decorative paints or marine antifouling paints; coatings, such as clear coats; caulks; mastics; adhesives; plastics; wood and wood products.

The controlled release compositions of the present invention are especially useful in paints, where the metal oxide glass or organo-metal oxide glass may also function as a pigment or opacifier. Compositions of the present invention that are particularly useful as pigments or opacifiers are those prepared from titanium alkoxide monomers.

When compositions of the present invention comprise a microbicide, they can either be added directly to the locus to be protected or added as a composition further comprising a suitable carrier. Suitable carriers useful for microbicidal applications include, but are not limited to, water; organic solvent; or mixtures thereof Suitable organic solvents include, but are not limited to: ethylene glycol, diethylene glycol, propylene glycol, dipropylene glycol, xylene, toluene, acetone, methyl iso-butyl ketone, and esters. The compositions may also be formulated as microemulsions, microemulsifiable concentrates, emulsions, emulsifiable concentrates, pastes, or may be encapsulated. The particular formulation will depend upon the locus to be protected and the particular microbicide used. The preparation of these formulations is by well known, standard methods.

The amount of the compositions of the present invention necessary to control or inhibit the growth of microorganisms depends upon the locus to be protected, but is typically sufficient if it provides from 0.5 to 2500 ppm of microbicide, at the locus to be protected. Microbicides are often used in loci that require further dilution. For example, the compositions of the invention may be added to a metal working fluid concentrate, which is then further diluted. The amount of the compositions of the invention necessary to control microorganism growth in the final metal working fluid dilution are sufficient if they provide generally from 5 to 50 ppm of the microbicide in the final dilution. In loci such as a paint, which is not further diluted, the amount of the compositions of the invention necessary to control microorganism growth are sufficient if they provide generally from 500 to 2500 ppm of the microbicide.

When the biologically active compound of the present invention is a marine antifouling agent, the compositions of the present invention can be used to inhibit the growth of marine organisms by application of the compositions onto or into a marine structure. Depending upon the particular marine structure to be protected, the compositions of the present invention can be directly incorporated into the marine structure, applied directly to the marine structure, or incorporated into a coating which is then applied to the marine structure.

Suitable marine structures include, but are not limited to: boats, ships, oil platforms, piers, pilings, docks, elastomeric rubbers, and fish nets. The compositions of the present invention are typically directly incorporated into structures such as elastomeric rubber or fish net fibers during manufacture. Direct application of the compositions of the invention is typically made to structures such as fish nets or wood pilings. The compositions of the invention can also be incorporated into a marine coating, such as a marine paint or varnish.

When the compositions of the present invention comprise a marine antifouling agent, the amount of the compositions of the invention necessary to inhibit or prevent the growth of marine organisms is typically sufficient if it provides from 0.1 to 30 wt % of marine antifouling agent alone, based on the weight of the structure to be protected or based on the weight of the coating to be applied. When the compositions of the invention are directly incorporated into or directly applied onto a structure, the amount of the compositions necessary to inhibit the growth of marine organisms is generally sufficient if it provides 0.1 to 30 wt % of marine antifouling agent alone, based on the weight of the structure. It is preferred that the amount of the compositions of the invention be sufficient to provide 0.5 to 20 wt % of marine antifouling agent alone; more preferably, 1 to 15 wt %. When incorporated into a coating, the amount of the compositions of the invention suitable to inhibit the growth of marine organisms is generally sufficient if it provides 0.1I to 30 wt % of marine antifouling agent alone, based on the weight of said coating. The amount of the compositions of the invention preferably provides 0.5 to 15 wt % of marine antifouling agent alone; more preferably, 1 to 10 wt %.

In general, the compositions of the present invention comprising a marine antifouling agent are incorporated in a carrier such as water; organic solvent, such as xylene, methyl isobutyl ketone, and methyl isoamyl ketone; or mixtures thereof.

Direct applications of the compositions of the present invention may be by any conventional means, such as dipping, spraying, or coating. Fish nets, for example, may be also protected by dipping the fish nets into a composition comprising the compositions of the invention and a carrier or by spraying the fish nets with said composition.

Structures such as wood pilings and fish nets may be protected by directly incorporating the compositions of the invention into the structure. For example, a compostion of the invention further comprising a carrier may be applied to wood used for pilings by means of pressure treatment or vacuum impregnation. These compositions may also be incorporated into a fish net fiber during manufacture.

Marine coatings comprise a binder and solvent and optionally other ingredients. The solvent may be either organic solvent or water. The compositions of the present invention are suitable for use in both solvent- and water-based marine coatings. Solvent-based marine coatings are preferred.

Any conventional binder may be utilized in the marine antifouling coating incorporating the compositions of the present invention. Suitable binders include, but are not limited to: polyvinyl chloride in a solvent-based system; chlorinated rubber in a solvent based system; acrylic resins in solvent-based or aqueous systems; vinyl chloride-vinyl acetate copolymer systems as aqueous dispersions or solvent-based systems; butadiene-styrene rubbers; butadiene-acrylonitrile rubbers; butadiene-styrene-acrylonitrile rubbers; drying oils such as linseed oil; asphalt; epoxies; siloxanes; and the like.

The marine coatings of the present invention may optionally contain one or more of the following: inorganic pigments, organic pigments, or dyes, and controlled release materials, such as rosin. Water-based coatings may also optionally contain: coalescents, dispersants, surface active agents, rheology modifiers, or adhesion promoters. Solvent-based coatings may also optionally contain extenders, plasticizers, or rheology modifiers.

A typical marine coating comprises 2 to 20 wt % binders, up to 15 wt % rosins/modified rosins, 0.5 to 5 wt % plasticizers, 0.1 to 2 wt % antisettling agent, 5 to 60 wt % solvent/diluent, up to 70 wt % cuprous oxide, up to 30 wt % pigments (other than cuprous oxide), and up to 15 wt % marine antifouling agent.

Marine coatings containing the compositions of the present invention may be applied to a structure to be protected by any of a number of conventional means. Suitable means of application include, but are not limited to, spraying; rolling; brushing; or dipping.

When the biologically active compound is an agricultural pesticide, the compositions of the present invention may be applied to plants or soil or may be used as seed treatments. The compositions may be used directly or formulated as dusts, granules, flowables, emulsifiable concentrates, microemulsifiable concentrates, emulsions, microemulsions, or may be encapsulated.

The following examples are presented to illustrate further various aspects of the present invention, but are not intended to limit the scope of the invention in any aspect.

EXAMPLES 1–47

The following are examples of compositions of the present invention prepared according to the following general methods.

Metal Oxide Glass—Method A

Metal alkoxide monomer(s), biologically active compound, and water were combined in a flask. The mole ratio of metal alkoxide monomer to water was 1:2. The amount of biologically active compound was such that the final product contained from 2–50 wt %. This reaction mixture was homogenized by adding methanol or ethanol while stirring. A catalytic amount of dilute hydrochloric acid (8–10 g of 0.01N HCl per mole of metal alkoxide monomer) was then added to the reaction mixture. The reaction mixture was allowed to polymerize at room temperature for 3 to 60 days. After polymerization, the volatile components were removed under reduced pressure to give a solid metal oxide glass containing the biologically active compound.

Metal Oxide Glass—Method B

The procedure of Method A was followed and inert material was added to the reaction mixture after polymerization, but before the volatile components were removed. This yielded a solid metal oxide glass containing the biologically active compound and inert material. The amount of inert material added was such that the resulting metal oxide glass contained 70 wt %, based on the final weight of the composition.

Organo-Metal Oxide Glass

Metal alkoxide monomer(s), biologically active compound, and water were combined in a flask. The mole ratio of metal alkoxide monomer to water was 1:2. The amount of biologically active compound was such that the final product contained from 5–50 wt %. The reaction mixture was homogenized by adding methanol or ethanol while stirring. A catalytic amount of dilute hydrochloric acid (8–10 g of 0.01N HCl per mole of metal alkoxide monomer) was then added to the reaction mixture. The reaction mixture was allowed to polymerize at room temperature for 3 to 60 days. After polymerization, 10–60 wt % of hydroxylic compound was added to the polymerized reaction mixture. The volatile components were then removed under reduced pressure to give a solid organo-metal oxide glass containing the biologically active compound.

The compositions prepared are reported in Table 1. All compositions in Table 1 were obtained as solids. The amount of biologically compound, inert material, and hydroxylic compound in the compositions is reported as wt %, based on the weight of the composition. The abbreviations used in Table 1 are as follows.

Metal Alkoxide Monomers:

TEOS Tetraethoxy orthosilicate
MTEOS Methyltriethoxy orthosilicate
PTEOS Phenyltriethoxy orthosilicate
OTEOS Octyltriethoxy orthosilicate
DMDEOS Dimethyldiethoxy orthosilicate
MTMOS Methyltrimethoxy orthosilicate
PTMOS Phenyltrimethoxy orthosilicate
TMOS Tetramethoxy orthosilicate Biologically Active Compounds:

C1 4,5-Dichloro-2-n-octyl-3-isothizaolone
C2 5-Chloro-2-methyl-3-isothiazolone and 2-methyl-3-isothiazolone in a 3:1 ratio.
C3 Iodopropynyl butyl carbamate
C4 2-Methylthio-4-t-butylamino-6-cyclopropylamino-s-triazine
C5 2',6'-Dibromo-2-methyl-4'-trifluoromethoxy-4-trifluoromethyl-1,3-thiazole-5-carboxanilide (also known as thifluzamide)

Hydroxylic Compound:

H1 Propylene glycol
H2 Methoxy(polyethylene) glycol MW = 350
H3 Methoxy(polyethylene) glycol MW = 750

Inert Material:

I1 Zirconium hydroxide
I2 Titanium dioxide
I3 Aluminum hydroxide
I4 para-Cresol
I5 Dextrane (a polysaccharide)
I6 Phenol-formaldehyde condensate having MW = 2000 (Phenyl Novolac SD-1711)

TABLE 1

| Example | Metal Alkoxide A | Monomer B | Mole Ratio A:B | Inert (wt %) | Biologically Active Compound (% wt) | Hydroxylic Compound (% wt) |
|---|---|---|---|---|---|---|
| 1 | TEOS | MTEOS | 4:1 | — | C1 (5) | — |
| 2 | " | " | 1:1 | — | C1 (5) | — |
| 3 | " | " | 1:4 | — | C1 (5) | — |
| 4 | TMOS | MTMOS | 1:1 | — | C1 (5) | — |
| 5 | MTEOS | — | — | — | C1 (12) | — |
| 6 | MTEOS | — | — | — | C1 (30) | — |
| 7 | MTEOS | — | — | — | C1 (48) | — |
| 8 | OTEOS | — | — | — | C1 (8) | — |
| 9 | TEOS | OTEOS | 1:1 | — | C1 (8) | — |
| 10 | TEOS | OTEOS | 9:1 | — | C1 (11) | — |
| 11 | DMDEOS | — | — | — | C1 (21) | — |
| 12 | DMDEOS | TEOS | 1:1 | — | C1 (10) | — |
| 13 | DMDEOS | TEOS | 1:9 | — | C1 (10) | — |
| 14 | MTEOS | — | — | — | C1 (10) | — |
| 15 | TEOS | MTEOS | 1:4 | — | C1 (12) | — |
| 16 | TEOS | PTEOS | 1:1 | — | C1 (11) | — |
| 17 | MTEOS | — | — | — | C1 (7) | H1 (50) |
| 18 | MTEOS | — | — | — | C1 (11) | H1 (50) |
| 19 | MTEOS | — | — | — | C1 (6) | H2 (50) |
| 20 | MTEOS | — | — | — | C1 (12) | H2 (50) |
| 21 | TEOS | PTEOS | 1:9 | — | C1 (7) | — |
| 22 | TEOS | PTEOS | 20:1 | — | C1 (11) | — |
| 23 | TEOS | PTEOS | 9:1 | — | C1 (25) | — |
| 24 | MTEOS | — | — | — | C1 (8) | — |
| 25 | MTEOS | — | — | — | C3 (9) | — |
| 26 | TEOS | PTEOS | 1:1 | — | C1 (8) | — |
| 27 | TEOS | PTEOS | 9:1 | — | C1 (11) | — |
| 28 | MTEOS | — | — | — | C5 (12) | — |
| 29 | MTEOS | — | — | — | C4 (12) | — |
| 30* | MTEOS | — | — | — | C1 (2) | — |
| 31 | TEOS | PTEOS | 1:1 | — | C1 (9)+ C2 (10) | — |
| 32* | MTEOS | — | — | — | C1 (2) | — |

TABLE 1-continued

| Example | Metal Alkoxide A | Monomer B | Mole Ratio A:B | Inert (wt %) | Biologically Active Compound (% wt) | Hydroxylic Compound (% wt) |
|---|---|---|---|---|---|---|
| 33* | TEOS | PTEOS | 1:1 | — | C1 (2) | — |
| 34 | MTMOS | — | — | — | C1 (20) | — |
| 35 | MTMOS | — | — | — | C1 (50) | — |
| 36 | TMOS | PTMOS | 1:1 | — | C1 (20) | — |
| 37 | TMOS | PTMOS | 1:1 | — | C1 (50) | — |
| 38 | PTMOS | — | — | — | C1 (50) | — |
| 39 | MTEOS | — | — | — | C1 (19) | H2 (60) |
| 40 | MTEOS | — | — | — | C1 (25) | H3 (50) |
| 41 | TEOS | — | — | — | C2 (13) | H3 (18) |
| 42 | MTMOS | — | — | I1 (70) | C1 (15) | — |
| 43 | MTMOS | — | — | I2 (70) | C1 (15) | — |
| 44 | MTMOS | — | — | I3 (70) | C1 (15) | — |
| 45 | MTMOS | — | — | I4 (70) | C1 (15) | — |
| 46 | MTMOS | — | — | I5 (70) | C1 (15) | — |
| 47 | MTMOS | — | — | I6 (70) | C1 (15) | — |

*Ethanol solvent was not removed from these samples.

EXAMPLE 48

A metal oxide glass composition of the present invention was formulated in a plasticizer.

MTEOS (9.2 g), 4,5-dichloro-2-n-octyl-3-isothiazolone (1.1 g), and water (1.9 g) were combined in a flask. This reaction mixture was homogenized by adding 6.6 g of ethanol while stirring. A catalytic amount of hydrochloric acid (0.5 g of a 0.1N solution) was added and the mixture allowed to polymerize at room temperature. After polymerizing for four days, 8.8 g of diisodecylphthalate was added to the reaction mixture. The volatile components were then removed under reduced pressure to yield a two-phase, liquid composition. This composition contained 8.2 wt % of 4,5-dichloro-2-n-octyl-3-isothiazolone.

These data clearly show that the compositions of the present invention can be formulated as a liquid composition.

EXAMPLE 49

The compositions of Examples 1–47 were evaluated for their rate of release of the biologically active compound according to the following procedure.

A weighed amount of a sample was placed in a 100 mL sample jar. To the jar was then added 100 mL of water containing 0.2% wt of sodium octylsulfosuccinate. The solution was then gently stirred to ensure no foam was formed. Aliquots (0.5 mL) were taken at various time points and transferred to a microcentrifuge tube. Each aliquot was then centrifuged at 14,000 rpm for 3 minutes. The supernatent was then removed and analyzed by HPLC for the amount of the biologically active compound. The microcentrifuge tube was then washed with 0.5 mL of water containing 0.2% wt of sodium octylsulfosuccinate and the wash liquid added to the sample jar. This ensured that none of the particles removed during sampling were lost and that the volume in the jar remained constant. The cumulative percentages of 4,5-dichloro-2-n-octyl-3-isothiazolone released are reported in Table 2.

TABLE 2

| Amount of 4,5-Dichloro-2-n-octyl-3-isothiazolone (% wt) | | | | | | | | | |
|---|---|---|---|---|---|---|---|---|---|
| Time (hrs) | 0 | 0.5 | 2 | 20 | 31 | 92 | 96 | 140 | 144 |
| Example 1 | 5 | 30 | 41 | — | 50 | — | — | — | 64 |
| Example 2 | 5 | 7 | 13 | — | 20 | — | — | — | 26 |
| Example 3 | 5 | 0.3 | 0.4 | — | 2 | — | — | — | 4 |
| Example 5 | 12 | 3 | 6 | — | 18 | — | 27 | — | — |
| Example 6 | 30 | 1 | 5 | — | 32 | — | 53 | — | — |
| Example 7 | 48 | 2 | 7 | — | 38 | — | 57 | — | — |
| Example 21 | 7 | — | — | 7.5 | — | 9.2 | — | 10.4 | — |
| Example 26 | 8 | — | — | 10.3 | — | 14.1 | — | 18.3 | — |
| Example 27 | 11 | — | — | 27.8 | — | 55.8 | — | 69.3 | — |

These data clearly show that the release rate of a biologically active compound can be controlled by changing the metal alkoxide monomers used to form the compositions of the present invention.

EXAMPLE 50

The particle size of the compositions of Examples 1–47 were measured. A small amount of sample was placed in a container of water attached to a Coulter counter. A water-soluble, non-ionic surfactant was then added to the container to disperse the sample particles. Once the particles were dispersed, the particle size was determined by laser diffraction. The results are reported in Table 3.

TABLE 3

| Particle Size | Example 26 | Example 27 |
|---|---|---|
| Mean | 23.5 μm | 89.1 μm |
| Median | 31 μm | 204 μm |
| Mode | 55 μm | 269 μm |

The mode is the particle size of most of the particles. From these data, and the leach rates in Example 49, it can be seen that the release rate of the biologically active compounds from the compositions of the present invention is not dependent upon the particle size. The rate of release of the biologically active compound is instead related to the particular monomers used to prepare the compositions of the present invention.

What is claimed is:

1. A controlled release composition comprising one or more biologically active compounds incorporated into a metal oxide glass having a porous matrix, wherein:

(a) the biologicaillty active compound is selected from the group consisting of microbicide, marine antifouling agent, and agricultural pesticide; and (b) the metal oxide glass is prepared by polymerizing one or more metal alkoxide monomers of formula (I)

$(R^2)_n M_1^{+m} (OR^1)_3$        (I)

optionally in the presence of one or more metal alkoxide monomers of formula (II)

$(R^5)_y R^4 R^3 M_2^{30-x} OR^1$        (II)

wherein:

$M_1$ and $M_2$ are independently selected from Silicon, aluminum, zirconium, titanium, tin, vanadium, and iron; $R^1 = (C_{1-4})$, ailyl; $R^2$, $R^3$, $R^4$ and $R^5$ are independently selected from OR¹, (C₁₋₁₂)alkyl, substituted (C₁₋₁₂)alkyl, (C₂₋₁₀)alkenyl, halosubstitutod (C₂₋₁₀) atlkenyl, (C₃₋₁₀)alkyiiyl, halosubstituted (C₃₋₁₀) alkynyl, phenyl, substituted phenyl, (C₇₋₁₀)aralkyl; m and x are independently 3 or 4; n=m-3; and y=x-3;

with the proviso that at least one of R², R³, or R⁵ must be present and is other than OR¹; and with the proviso that when the biologically active compound is an agricultural pesticide, at least one metal alkoxide monomer of formula (II) is present where R³ or R⁴ is not OR¹.

2. The composition of claim 1 wherein the biologically active compound is a microbicide or marine antifouling agent selected from the group consisting of: 5-chloro-2-methyl-3-isothiazolone; 2-methyl-3-isothiazolone; 2-n-octyl-3-isothiazolone; 4,5-dichloro-2-n-octyl-3-isothiazolone; 4,5-dichloro-2-cyclohexyl-3-isothiazolone; 4,5-dichloro-2-cyclohexyl-3-isothiazolone; 3-iodo-2-propynyl butyl carbamate; 1,2-dibromo-2,4-dicyanobutane; methylene-bis-thiocyanate; 2-thiocyanomethylthiobenzothiazole; 2,4,5,6-tetrachloroisophthalonitrile; 5-bromo-5-nitro-1,3-dioxane; 2,2-dibromo-3-nitrilopropionamide; 3-bromo-1-chloro-5,5-dimethylhydantoin; 1,2-benzisothiazolin-3-one; 2-methyl-4, 5-trimethylene-3-isothiazolone; 3,4,4'-trichlorocarbanilide; manganese ethylenebisdithiocarbamate; zinc dimethyl dithiocarbamate; 2-methyl-4-t-butylamino-6-cyclopropylamino-s-triazine; 2,4,5,6-tetrachloroisophthalonitrile; N,N-dimethyl dichlorophenyl urea; zinc ethylenebisdithiocarbamate; copper thiocyanate; 4,5-dichloro-2-n-octyl-3-isothiazolone; N-(fluorodichloromethylthio)-phthalimide; N,N-dimethyl-N'-phenyl-N'-fluorodichloromethylthio-sulfamide; zinc 2-pyridinethiol-1-oxide; tetramethylthiuram disulfide; 2,4,6-trichlorophenylmaleimide; 2 3,5,6-tetrachloro-4-(methylsulfonyl)-pyridine; 3-iodo-2-propynyl butyl carbamate; diiodomethyl p-tolyl sulfone; bis dimethyl dithiocarbamoyl zinc ethylenebisdithiocarbamate; phenyl (bispyridil) bismuth dichloride; 2-(4-thiazolyl)-benzimidazole; pyridine triphenyl borane; phenylamides; halopropargyl compounds; and 2-haloalkoxyaryl-3-isothiazolones.

3. The composition of claim 2 wherein the biologically active compound is a microbicide selected from the group consisting of: 2-methyl-3-isothiazolone; 5-chloro-2-methyl-3-isothiazolone; 2-n-octyl-3-isothiazolone; 4,5-dichloro-2-n-octyl-3-isothiazolone; 4,5-dichloro-2-cyclohexyl-3-isothiazolone; 1,2-benzisothiazolin-3-one; 2-methyl-4,5-trimethylene-3-isothiazolone; 3-iodo-2-propynyl butyl carbamate; and 3,4,4'-trichlorocarbanilide.

4. The composition of claim 1 wherein the metal alkoxide monomer of Formula II is selected from the group consisting of: tetramethoxy orthosilicate, tetraethoxy orthosilicate, methyltriethoxy orthosilicate, methyltrimethoxy orthosilicate, phenyltriethoxy orthosilicate, octyltriethoxy orthosilicate, phenyltrimethoxy orthosilicate, dimethyldiethoxy orthosilicate, bis(trimethoxysilyl)methane, bis(triethoxysilyl)ethane, bis(trimethoxysilyl)hexane, 3-butenyltriethoxy silane, methacryloxypropyl triethoxysilane, methacryloxypropyl trimethoxysilane, triethoxyaluminum, methyldiethoxyaluminum, triusopropoxyaluminum, tetraethoxyzirconium, methyltriethoxyzirconium, tetran-butoxyzirconium, tetra-t-butoxyzirconium, tetramethoxytin, tetraethoxytin, tetramethoxyvanadium, tetraethoxyvanadium, tetraethoxytitanium, tetramethoxytitanium, tetraethoxyiron, and mixtures thereof.

5. The composition of claim 1 wherein the biologically active compound is an agricultural pesticide selected from the group consisting of: dithiocarbamate derivatives; nitrophenol derivatives; heterocyclic structures; halogenated fungicides; fungicidal antibiotics; diphenyl sulfone; dodine; methoxyl; 1-thiocyano-2,4-dinitrobenzene; 1-phenylthiosemicarbazide; thiophanate-methyl; cymoxanil; acylalanines; phenylbenzamide; amino acid derivatives; methoxyacrylates; propamocarb; imazalil; carbendazim; myclobutanil; fenbuconazole; tridemorph; pyrazophos; fenarimol; fenpiclonil; pyrimethanil; carboxylic acid derivatives; carbamic acid derivatives; substituted ureas; substituted triazines; diphenyl ether derivatives; anilides; oxyphenoxy herbicides; uracils; nitriles; dithiopyr; thiazopyr; acephate; aldicarb; alpha-cypermethrin: azinphos-methyl; bifenthrin; binapacryl; buprofezin; carbaryl; carbofuran; cartap; chlorpyrifos; chlorpyrifos methyl; clofentezine; cyfluthrin; cyhexatin; cypermethrin; cyphenothrin; deltamethrin; demeton; demeton-S-methyl; demeton-O-methyl; demeton-S; demeton-S-methyl sulfoxid; demephion-O; demephion-S; dialifor; diazinon; dicofol; dicrotophos; diflubenzuron; dimethoate; dinocap; endosulfan; endothion; esfenvalerate; ethiofencarb; ethion; ethoate-methyl; ethoprop; etrimfos; fenamiphos; fenazaflor; fenbutatin-oxide; fenitrothion; fenoxycarb; fensulfothion; fenthion; fenvalerate; flucycloxuron; flufenoxuron; fluvalinate; fonofos; fosmethilan; furathiocarb; hexythiazox; isazophos; isofenphos; isoxathion; methamidophos; methidathion; methiocarb; methomyl; methyl parathion; mevinphos; mexacarbate; monocrotophos; nicotine; omethoate; oxamyl; parathion; permethrin; phorate; phosalone; phosmet; phosphamidon; pirimicarb; pirimiphosethyl; profenofos; promecarb; propargite; pyridaben; resmethrin; rotenone; tebufenozide; temephos; TEPP; terbufos; thiodicarb; tolclofos-methyl; triazamate; triazophos; and vamidothion.

6. The composition of claim 1 further comprising an inert material.

7. A controlled release composition comprising one or more biologically active compounds incorporated into an organo-metal oxide glass having a porous matrix, wherein: the biologically active compound is selected from the group consisting of microbicide, marine antifouling agent, and agricultural pesticide; and the organo-metal oxide glass is prepared by polymerizing, in the presence of a hydroxylic compound which is incorporated into polymer as a crosslinking or a pendant group, one or more metal alkoxide monomers of formula (I);

(I)

optionally in the presence of one or more metal alkoxide mionomers of formula (II):

(II)

wherein; $M_1$ and $M_2$ are independently selected from silicon, aluminum, zirconium, titanium, tin, vanadium, and iron; $R^1=(C_{1-4})$alkyl; $R^2$, $R^3$, $R^4$ and $R^5$ are independently selected from OR¹, (C₁₋₁₂)alkyl, substituted (C₁₋₁₂))alkyl, (C₂₋₁₀)alkrenyl, halosubstituted (C₂₋₁₀)alkenyl, (C₃₋₁₀) alkynyl, halosubtittuted (C₃₋C₁₀)alkynyl, phenyl, substituted phonyl, (C₇₋₁₀)aralkyl; m and x are independently 3 or 4; n=m-3; and y=x-3; and wherein the hydroxylic compound is selected from the group consisting of (C₄₋₂₀)alkyl alcohols; (C₇₋₁₀)aralkyl alcohols; (C₂₋₂₀)glycols; poly(ethylene glycol) alkyl ethers; polyethylene glycol) aralkyl ethers; and poly(ethylene glycol) Bryl ethers.

8. The composition of claim 7 wherein the biologically active compound is selected from the group consisting of:

5-chloro-2-methyl-3-isothiazolone; 2-methyl-3-isothiazolone; 2-n-octyl-3-isothiazolone; 4,5-dichloro-2-n-octyl-3-isothiazolone; 4,5-dichloro-2-cyclohexyl-3-isothiazolone; 4,5-dichloro-2-cyclohexyl-3-isothiazolone; 3-iodo-2-propynyl butyl carbamate; 1,2-dibromo-2,4-dicyanobutane; methylene-bis-thiocyanate; 2-thiocyanomethylthiobenzothiazole; 2,4,5,6-tetrachloroisophthalonitrile; 5-bromo-5-nitro-1,3-dioxane; 2,2-dibromo-3-nitrilopropionamide; 3-bromo-1-chloro-5,5-dimethylhydantoin; 1,2-benzisothiazolin-3-one; 2-methyl-4, 5-trimethylene-3-isothiazolone; 3,4,4'-trichlorocarbanilide; dithiocarbamate derivatives; nitrophenol derivatives; heterocyclic structures; halogenated fungicides; fungicidal antibiotics; diphenyl sulfone; dodine; methoxyl; 1-thiocyano-2, 4-dinitrobenzene; 1-phenylthio-semicarbazide; thiophanate-methyl; cymoxanil; acylalanines; phenylbenzamide; amino acid derivatives; methoxyacrylates; propamocarb; imazalil; carbendazim; myclobutanil; fenbuconazole; tridemorph; pyrazophos; fenarimol; fenpiclonil; pyrimethanil; carboxylic acid derivatives; carbamic acid derivatives; substituted ureas; substituted triazines; diphenyl ether derivatives; anilides; oxyphenoxy herbicides; uracils; nitriles; dithiopyr; thiazopyr; acephate; aldicarb; alpha-cypermethrin; azinphos-methyl; bifenthrin; binapacryl; buprofezin; carbaryl; carbofuran; cartap; chlorpyrifos; chlorpyrifos methyl; clofentezine; cyfluthrin; cyhexatin; cypermethrin; cyphenothrin; deltamethrin; demeton; demeton-S-methyl; demeton-O-methyl; demeton-S; demeton-S-methyl sulfoxid; demephion-O; demephion-S; dialifor; diazinon; dicofol; dicrotophos; diflubenzuron; dimethoate; dinocap; endosulfan; endothion; esfenvalerate; ethiofencarb; ethion; ethoate-methyl; ethoprop; etrimfos; fenamiphos; fenazaflor; fenbutatin-oxide; fenitrothion; fenoxycarb; fensulfothion; fenthion; fenvalerate; flucycloxuron; flufenoxuron; fluvalinate; fonofos; fosmethilan; furathiocarb; hexythiazox; isazophos; isofenphos; isoxathion; methamidophos; methidathion; methiocarb; methomyl; methyl parathion; mevinphos; mexacarbate; monocrotophos; nicotine; omethoate; oxamyl; parathion; permethrin; phorate; phosalone; phosmet; phosphamidon; pirimicarb; pirimiphos-thyl; profenofos; promecarb; propargite; pyridaben; resmethrin; rotenone; tebufenozide; temephos; TEPP; terbufos; thiodicarb; toldlofos-methyl; triazamate; triazophos; and vamidothion.

9. The composition of claim 7 wherein the biologically active compound is a microbicide selected from the group consisting of: 2-methyl-3-isothiazolone; 5-chloro-2-methyl-3-isothiazolone; 2-n-octyl-3-isothiazolone; 4,5-dichloro-2-n-octyl-3-isothiazolone; 4,5-dichloro-2-cyclohexyl-3-isothiazolone; 1,2-benzisothiazolin-3-one; 2-methyl-4,5-trimethylene-3-isothiazolone; 3-iodo-2-propynyl butyl carbamate; and 3,4,4'-trichlorocarbanilide.

10. A method of controlling the release of biologically active compounds comprising the step of incorporating the biologically active compounds in a metal oxide glass having a porous matrix, wherein:
(a) the biologically active compound is selected from the group consisting of microbicide, marine antifouling agent, and agricultural pesticide, and
(b) the metal oxide glass is prepared by polymerizing one or more metal alkoxide monomers of formula (I)

optionally in the presence of one or more metal alkoxide monomers of formula (II).

wherein $M_1$ and $M2$ are independently selected from silicon, aluminum, zirconium, titanium, tin, vanadium, and iron; $R^1=(C_{1-4})$alkyl; $R^2$, $R^3$, $R^4$ and $R^5$ are independently selected from $OR^1$, $(C_{1-12})$alkyl, substitiuted $(C_{1-12})$alkyl, $(C_{2-10})$alkJenyl, halosubstituted $(C_{2-10})$ alkonyl, $(C_{3-10})$ alkynyl, halosubstituted $(C_{3-10})$alkynyl, phenyl, substituted phonyl, $(C_{7-10})$aralkyl; m and x are independently 3 or 4; n=m-3; and y=x-3;
with the provision that at least one of $R^2$, $R^3$, $R^4$ or $R^5$ must be present and is other than $OR^1$; and
with the provision that when the biologically active compound is an agricultural pesticide, at least one metal alkoxide monomer of formula (II) is present where $R^3$ or $R^4$ is not $OR^1$.

11. The method of claim 10 wherein the biologically active compound is selected from the group consisting of 5-chloro-2-methyl-3-isothiazolone; 2-methyl-3-isothiazolone; 2-n-octyl-3-isothiazolone; 4,5-dichloro-2-n-octyl-3-isothiazolone; 4,5-dichloro-2-cyclohexyl-3-isothiazolone; 4,5-dichloro-2-cyclohexyl-3-isothiazolone; 3-iodo-2-propynyl butyl carbamate; 1,2-dibromo-2,4-dicyanobutane; methylene-bis-thiocyanate; 2-thiocyanomethylthiobenzothiazole; 2,4,5,6-tetrachloroisophthalonitrile; 5-bromo-5-nitro-1,3-dioxane; 2,2-dibromo-3-nitrilopropionamide; 3-bromo-1-chloro-5,5-dimethylhydantoin; 1,2-benzisothiazolin-3-one; 2-methyl-4, 5-trimethylene-3-isothiazolone; 3,4,4'-trichlorocarbanilide; dithiocarbamate derivatives; nitrophenol derivatives; heterocyclic structures; halogenated fungicides; fungicidal antibiotics; diphenyl sulfone; dodine; methoxyl; 1-thiocyano-2, 4-dinitrobenzene; 1-phenylthiosemicarbazide; thiophanate-methyl; cymoxanil; acylalanines; phenylbenzamide; amino acid derivatives; methoxyacrylates; propamocarb; imazalil; carbendazim; myclobutanil; fenbuconazole; tridemorph; pyrazophos; fenarimol; fenpiclonil; pyrimethanil; carboxylic acid derivatives; carbamic acid derivatives; substituted ureas; substituted triazines; diphenyl ether derivatives; anilides; oxyphenoxy herbicides; uracils; nitriles; dithiopyr; thiazopyr; acephate; aldicarb; alpha-cypermethrin; azinphos-methyl; bifenthrin; binapacryl; buprofezin; carbaryl; carbofuran; cartap; chlorpyrifos; chlorpyrifos methyl; clofentezine; cyfluthrin; cyhexatin; cypermethrin; cyphenothrin; deltamethrin; demeton; demeton-S-methyl; demeton-O-methyl; demeton-S; demeton-S-methyl sulfoxid; demephion-O; demephion-S; dialifor; diazinon; dicofol; dicrotophos; diflubenzuron; dimethoate; dinocap; endosulfan; endothion; esfenvalerate; ethiofencarb; ethion; ethoate-methyl; ethoprop; etrimfos; fenamiphos; fenazaflor; fenbutatin-oxide; fenitrothion; fenoxycarb; fensulfothion; fenthion; fenvalerate; flucycloxuron; flufenoxuron; fluvalinate; fonofos; fosmethilan; furathiocarb; hexythiazox; isazophos; isofenphos; isoxathion; methamidophos; methidathion; methiocarb; methomyl; methyl parathion; mevinphos; mexacarbate; monocrotophos; nicotine; omethoate; oxamyl; parathion; permethrin; phorate; phosalone; phosmet; phosphamidon; pirimicarb; pirimiphos-ethyl; profenofos; promecarb; propargite; pyridaben; resmethrin; rotenone; tebufenozide; temephos; TEPP; terbufos; thiodicarb; tolclofos-methyl; triazamate; triazophos; and vamidothion.

12. A method of controlling the release of biologically active compounds comprising the step of incorporating the biologically active compounds in an organo-metal oxide glass having a porous matrix, wherein; the biologically active compound is selected from the group consisting of microbicide, marine antifouling agent, and agricultural pesticide; and the organo-metal oxide glass is prepared by polymerizing, in the presence of a hydroxylic compound which is incorporated into the polymer as a crosslinking or a pendant group, one or more metal alkoxide monomers of formula (I):

$$(R^2)_n M_1 M_1^{+m}(OR^1)_3 \qquad (I)$$

optionally in the presence of one or more metal alkoxide mionomers of formula (II):

$$(R^5)_y R^4 R^3 M_2^{+x} OR^1 \qquad (II)$$

wherein $M_1$ and $M_2$ are independently selected from silicon, aluminum, zirconium, titanium, tin, vanadium, and iron; $R^1=(C_{1-4})$alkyl; $R^2$, $R^3$, $R^4$ and $R^5$ are independently selected from $OR^1$, $(C_{1-12})$alkyl, substituted $(C_{1-12})$allkyl, $(C_2$-$C_{10})$alkenyl, halosubstituted $(C_{2-10})$ alkenyl, $(C_{3-10})$ alkynyl, halosubstituted $(C_{3-10})$alkynyl, phenyl, substituted phenyl, $(C_{7-10})$aralkyl; m and x are independently 3 or 4, n=m-3; and y=x-3; and wherein the hydroxylic compound is selected from the group consisting of $(C_{4-20})$alkyl alcohols; $(C_{7-10})$aralkyl alcohols; $(C_{2-20})$glycols; poly(ethylene glycol) alkyl ethers; poly(ethylene glycol) aralkyl others; and poly(ethylene glycol) aryl ethers.

13. The method of claim 12 wherein the biologically active compound is selected from the group consisting of: 5-chloro-2-methyl-3-isothiazolone; 2-methyl-3-isothiazolone; 2-n-octyl-3-isothiazolone; 4,5-dichloro-2-n-octyl-3-isothiazolone; 4,5-dichloro-2-cyclohexyl-3-isothiazolone; 4,5-dichloro-2-cyclohexyl-3-isothiazolone; 3-iodo-2-propynyl butyl carbamate; 1,2-dibromo-2,4-dicyanobutane; methylene-bis-thiocyanate; 2-thiocyanomethylthiobenzothiazole; 2,4,5,6-tetrachloroisophthalonitrile; 5-bromo-5-nitro-1,3-dioxane; 2,2-dibromo-3-nitrilopropionamide; 3-bromo-1-chloro-5,5-dimethylhydantoin; 1,2-benzisothiazolin-3-one; 2-methyl-4, 5-trimethylene-3-isothiazolone; 3,4,4'-trichlorocarbanilide; dithiocarbamate derivatives; nitrophenol derivatives; heterocyclic structures; halogenated fungicides; fungicidal antibiotics; diphenyl sulfone; dodine; methoxyl; 1-thiocyano-2,4-dinitrobenzene; 1-phenylthio-semicarbazide; thiophanate-methyl; cymoxanil; acylalanines; phenylbenzamide; amino acid derivatives; methoxyacrylates; propamocarb; imazalil; carbendazim; myclobutanil; fenbuconazole; tridemorph; pyrazophos; fenarimol; fenpiclonil; pyrimethanil; carboxylic acid derivatives; carbamic acid derivatives; substituted ureas; substituted triazines; diphenyl ether derivatives; anilides; oxyphenoxy herbicides; uracils; nitriles; dithiopyr; thiazopyr; acephate; aldicarb; alpha-cypermethrin; azinphos-methyl; bifenthrin; binapacryl; buprofezin; carbaryl; carbofuran; cartap; chlorpyrifos; chlorpyrifos methyl; clofentezine; cyfluthrin; cyhexatin; cypermethrin; cyphenothrin; deltamethrin; demeton; demeton-S-methyl; demeton-O-methyl; demeton-S; demeton-S-methyl sulfoxid; demephion-O; demephion-S; dialifor; diazinon; dicofol; dicrotophos; diflubenzuron; dimethoate; dinocap; endosulfan; endothion; esfenvalerate; ethiofencarb; ethion; ethoate-methyl; ethoprop; etrimfos; fenamiphos; fenazaflor; fenbutatin-oxide; fenitrothion; fenoxycarb; fensulfothion; fenthion; fenvalerate; flucycloxuron; flufenoxuron; fluvalinate; fonofos; fosmethilan; furathiocarb; hexythiazox; isazophos; isofenphos; isoxathion; methamidophos; methidathion; methiocarb; methomyl; methyl parathion; mevinphos; mexacarbate; monocrotophos; nicotine; omethoate; oxamyl; parathion; permethrin; phorate; phosalone; phosmet; phosphamidon; pirimicarb; pirimiphos-ethyl; profenofos; promecarb; propargite; pyridaben; resmethrin; rotenone; tebufenozide; temephos; TEPP; terbufos; thiodicarb; tolclofos-methyl; triazamate; triazophos; and vamidothion.

14. A method of controlling or inhibiting the growth of pests at a locus comprising introducing into or onto the locus to be protected an effective amount of the compositions of claim 1.

15. A method of controlling or inhibiting the growth of pests at a locus comprising introducing into or onto the locus to be protected an effective amount of the compositions of claim 7.

* * * * *